United States Patent [19]

Tzodikov

[11] 4,432,877

[45] Feb. 21, 1984

[54] ORGANO-MERCURIAL MATERIALS

[75] Inventor: Nathan R. Tzodikov, Marshfield, Mass.

[73] Assignee: New England Nuclear Corporation, Boston, Mass.

[21] Appl. No.: 312,716

[22] Filed: Oct. 19, 1981

[51] Int. Cl.³ .............................................. B01D 15/08
[52] U.S. Cl. ................................ 210/656; 210/198.2; 502/401
[58] Field of Search ..................... 210/635, 656, 198.2, 210/302; 55/67, 386; 252/428, 430, 431, 449, 457, 459, 460, 465; 435/815

[56] References Cited

U.S. PATENT DOCUMENTS

| | | | |
|---|---|---|---|
| 2,106,744 | 2/1938 | Hood et al. | 210/502 |
| 3,485,687 | 12/1969 | Chapman | 65/31 X |
| 3,519,538 | 7/1970 | Messing . | |
| 3,795,313 | 3/1974 | Kirkland et al. | 210/502 |
| 4,329,254 | 5/1982 | Chmielowiec | 210/656 |

OTHER PUBLICATIONS

Organomercurial Agarose by Sluyterman and Wijdens in Methods of Enzymology 34:544 (Sc. Pros. 1974).
Affinity Purification of Synthetic Peptides by Krieger et al in Proc. Natl. Acad. Sci. USA 73:3160, 1976.
Rapid Separation of the Major Glycol Proteins . . . Affinity Chromatography by Shami et al. in Anal. Biochem. 80:438 (1977).
Encyclopedia of Chemical Technology by Kirk-Othmer, John Wiley and Sons, N.Y., vol. 2, pp. 586-609, also vol. 6, pp. 35-54, (3rd Ed. 1979).
Bonded Stationary Phases in Chromatography by Grushka, Ann Arbor Science Inc., Ann Arbor, Michigan, pp. 1-11, 1974.

*Primary Examiner*—John Adee
*Attorney, Agent, or Firm*—Sewall P. Bronstein; David G. Conlin

[57] ABSTRACT

Compositions in which organo-mercurial moieties are bound to glass or other inorganic substrates are useful in separating sulfhydryl-containing compounds from mixtures with other compounds, e.g., by affinity chromatography.

14 Claims, No Drawings

ORGANO-MERCURIAL MATERIALS

This invention relates to compositions in which organo-mercurial moieties are bound to glass or other inorganic substrates, and for methods of making and using the same, e.g., to separate sulfhydryl-containing compounds from non-sulfhydryl-containing compounds.

It has previously been known that many heavy metal ions, particularly mercury (II) ions have an attraction for organic compounds containing the sulfhydryl (SH) group. Many important organic materials contain the sulfhydryl group, such as the amino acid cysteine (and thus polypeptides such as proteins which contain cysteine), thiophosphorylated ribonucleoside triphosphates (RNA), thiophosphorylated deoxyribonucleoside triphosphates (DNA), as well as other compounds of industrial and pharmaceutical interest. One of the qualitative analysis tests for the sulfhydryl group has been the ability of sulfhydryls to form an insoluble precipitate when treated with heavy metal ions such as lead, silver, iron and mercury.

In the 70's, a product was developed in which a mercury compound was attached to a long chain polycarbohydrate (agarose), and the resultant product was utilized to remove sulfhydryls from certain mixtures with other compounds. The reaction involved cyanogen bromide activation of the polycarbohydrate chain at sites of occurrence of vicinal (i.e. 1,2) diols and reaction of the activated polymer with, e.g., p-aminophenylmercuric acetate. Thereafter the material was packed in a column and used to separate sulfhydryls from mixtures containing other compounds. See, e.g. Sluyterman et al, "Organomercurial Agarose", in Wilchek et al, *Methods in Enzymology*, 34:544 (Sc. Pros. 1974) which is hereby incorporated herein by reference.

However, the organo-mercurial-agarose compounds are inefficient, difficult to use, and unstable. The cyanogen bromide activation reaction is very low in efficiency, possibly partially because of the competition of solvents and other components in the reaction mixture with the 1,2 diols for reaction with cyanogen bromide, and possibly because of the amenability of the activated sites to attack, e.g., hydrolysis. There are a limited number of sites on the activated sugar molecules at which the mercurial compounds can be bonded, and thus such compositions are limited in the amount of sulfhydryl-containing compounds that they can pick up. This, plus the instability means that the compound is typically supplied at mercury levels substantially lower than those claimed by the manufacturer. Further, the high molecular weight sugars, which are in the form of a gel, are adversely affected by certain solvents, reactants, or other compounds in the solutions to be treated. For example, when treated with a composition containing a solvent for agarose, the material tends to become swollen and intractable, adversely affecting the column and the flow rate of eluant therethrough.

Despite these difficulties, the problems in separating sulfhydryls from other compounds were sufficiently difficult that a number of processes were developed for separating sulfhydryls from other compounds in a variety of compositions and circumstances. See, e.g., Krieger et al., "Affinity Purification of Synthetic Peptides," *Proc. Natl. Acad. Sci. USA* 73:3160 (1976), which is hereby incorporated by reference, Shami et al, "Rapid Quantitative Separation of the Major Glycol Proteins . . by Affinity Chromatography," *Anal. Biochem.* 80:438 (1977), also incorporated herein by reference.

It has now been found that excellent isolation of sulfhydryl-containing compounds from other compounds can be obtained with products which comprise particles of glass or other inorganic material to which certain organo-mercurial moieties have been bonded. These products in accordance with the invention are covalently bonded to glass or another inorganic carrier which has available hydroxyl or oxide groups. The mercury-bearing moiety is coupled to the inorganic carrier by means of a silane or other coupling agent, wherein the silicon portion of the molecule is attached to the inorganic carrier and the organic portion of the molecule is attached to the mercurial compound. This methodology gives an affinity product which has approximately 500% of the available mercury as compared with the typical agarose-based materials.

The carriers to be used in accordance with the present invention are preferably inorganic materials having available oxide or hydroxide groups. Preferably the materials are also siliceous materials, although they can also be non-siliceous metal oxides or hydroxides. Of the siliceous materials, the preferred is porous glass. By "porous glass", it is meant a boro-silicate glass, in particulate or other form, which has been treated or reacted to rid itself of boron. Such porous glass is readily commercially available, e.g., as sold by Corning Glass as Controlled Pore Glass. It is also available from Pierce Chemical Co. and Electronucleonics, Inc. Methods for making porous glass having various pore dimensions are disclosed in Hood et al U.S. Pat. No. 2,106,744 and Chapman et al U.S. Pat. No. 3,485,687, the disclosures of which are hereby incorporated by reference. Other siliceous inorganic carriers which can also be used include colloidal silica, wollastonite, dried silica gel, and bentonite. Useful non-siliceous metal oxides include alumina, hydroxy-apatite and nickel oxide.

The organo-mercurial moieties are bound to the glass or other inorganic carrier through a binding or coupling agent. The binding or coupling agent must be able to attach itself to the glass or other inert carrier, and must be readily reactable with the desired mercury moieties, so that, at one end of the molecule, it is bound to the inorganic carrier, and a mercury (II) atom is located at the other end of the molecule, which preferably projects out into the fluid stream. Sulfhydryl-containing compounds which are brought in contact with the carrier have an affinity for and thus are bound to the mercury (II) and removed from the fluid or mixture of compounds in which they are contained.

The coupling or bonding agent required by the invention is one which possesses different kinds of reactivity at each end of the molecule. The preferred coupling agents for use with this invention are silane coupling agents, which comprise a silicon portion, which has reactivity with inorganic materials such as glass, aluminum oxide or hydroxide or silicates, and an organic portion which is easily reactable with mercury compounds, e.g., mercury II salts or organo-mercury (II) compounds, so that organo-mercury moieties can be readily formed or attached at that end of the molecule. The inorganic-reactive end of the molecule is tailored to the inorganic material which will serve as the carrier base. The organic functional end of the coupling or bonding agent, should be tailored to react with whatever mercurial compound is to be used. A number of preferred types of silane type coupling agents are disclosed in the patent to Messing et al. U.S. Pat. No. 3,519,538, the disclosure of which is hereby incorporated herein by reference.

The preferred coupling agents for use in the present invention are organosilanes of the general formula:

$$(YR^1)_n Si(R^2)_{4-n} \qquad (1)$$

where Y is hydroxyl, amino, carboxylic acid and derivatives, e.g., acyl or acyloxy, preferably substituted or unsubstituted acryloxy, e.g., methacryloxy, isocyano, isothiocyano, sulfhydryl or a diazonium salt; $R^1$ is a member of the group of alkyl, preferably lower alkyl, lower alkenyl, lower alkyl-aryl, and aryl; $R^2$ is a member selected from the group consisting of lower alkoxy, substituted or unsubstituted phenoxy, and halo; and n is an integer having the value of 1–3. If there are more than one $R^1$, $R^2$ or Y group, each such group can be different from the others. If it is desired, $R^1$ can be left out of the above general formula. However, the preferred coupling agents are in accordance with the above formula, where $R^1$ is lower alkyl, and $R^2$ is lower alkoxy.

Y is simply a functional group which can react with a mercurial compound, to bind the mercury containing moiety to the coupling agent. The nature of that functional group depends on the nature of the mercury-containing moiety with which it is to be reacted. Preferably, Y is a methacryloxy group, which will react with mercury (II) salts such as mercuric acetate, mercuric halide or mercuric nitrate.

Generally the mercury can be derived from compounds having the following formula:

$$Z.Hg.Z^1 \qquad (2)$$

where Z and/or $Z^1$ can be anions, preferably the conjugate base of an acid, such as acetate, halide, including fluoride, chloride, bromide and iodide, cyanide, hydroxide, nitrate, oxylate, or other acid residues. Z and/or $Z^1$ can also be organic, such as alkyl, preferably lower alkyl, aryl, preferably phenyl or substituted phenyl, e.g., phenyl, or hydroxyphenyl, or other reactive groups known in the art. $Z^1$ and Z may be the same or may be different, and in the case of certain divalent anions, e.g., sulfate, the mercury (II) may simply be bound to one anion. The primary consideration is a reaction in which mercury will be in a covalent bond when attached to the coupling agent.

In the particularly preferred coupling agents, Y is acryloxy or substituted acryloxy, $R^1$ is lower alkyl, and $R^2$ is lower alkoxy. Such preferred coupling agents include
beta-acryloxyethyltrimethoxy silane;
gamma-acryloxypropyltrimethoxy silane;
gamma-acryloxypropyl-gamma-acryloxypropyldimethoxy silane;
delta-acryloxybutyltriethoxy silane;
gamma-acryloxypropyl-gamma-methacryloxypropyl ethoxymethoxy silane;
gamma-methacryloxypropyltrimethoxy silane;
gamma-methacryloxypropyl-beta-methacryloxyethyldimethoxy silane;
beta-methacryloxyethyl-(alpha-methyl-gamma-methacryloxypropyl)dimethoxy silane, and the like. At present, the most preferred coupling agent is gamma-methacryloxypropyltrimethoxy silane.

Preferably the coupling agent is applied to the glass or other inorganic substrate from a solvent solution at relatively high temperature, e.g., 50°–200° C. Typically this is done in a high boiling solvent at reflux conditions for a period of time ranging from about 1–20 hours, preferably between 3 and 18 hours, most preferably around 16 hours. Higher temperature favors the reaction, and thus the high boiling aromatic and aliphatic solvents are preferred, such as toluene, benzene, xylene, and high boiling hydrocarbons. Although the silane coupling agents are soluble in alcohol and water, their use as solvents is believed to interfere with the bonding obtained in the glass surface. It is also preferable to avoid the use of solvents which may react with the organic end of the coupling agents, such as amines or alkylthiols.

The compositions of the present invention are made by either attaching the coupling agent to the porous glass or other inorganic material, and then attaching the mercury to the coupling agent, or by forming a coupling agent having mercury at its organic terminus and then treating its other terminus with the hydroxide or oxides provided at the surface of the glass or other inorganic substrate. Preferably the mercury is added after the coupling agent is already attached to the glass, under conditions which will vary depending upon the type of mercury compound being used, and the type of coupling agent utilized. Where the mercury (II) compound is a salt, and Y in the above formula is the preferred methacryloxy-moiety, simple reaction at room temperature under an inert atmosphere is sufficient to bind the mercury (II) to the coupling agent and thus the glass. Other reactions may require more rigorous conditions, as will be appreciated by the skilled in the art.

While mercury is the most preferred and widely known compound having affinity for thiols, other metals having such affinity, such as lead, silver, gold, platinum, iron or tungsten, or having other affinities for other residues, can be utilized in accordance with the present invention.

Thus, the mercury/coupling agent/glass product of the present invention generally has the following formula:

$$G-Si(R^2)_{3-n}(R^1Y^1HgZ)_n \qquad (3)$$

wherein Z is as above defined, $Y^1$ is the residue of the functional group Y after reaction between the coupling agent of Formula (1) and the mercury compound of Formula (2), R1 and n are as above-defined, $R^2$ may be as above-defined, or may be involved in additional bridging linkages to the glass or other inorganic substrate surface, and G represents the binding site on the surface of the glass or other inorganic substrate, e.g., silicon or metal oxide or hydroxide. Where porous glass is used as the substrate, the porosity of the glass and particle size can vary considerably without affecting the basic properties of the material. Other solids, such as inorganic silicon or metal oxides bearing available oxide or hydroxide functions (e.g., silica gel, reprecipitated silica or alumina), or the others mentioned above, are capable of similar silanizations.

In a presently preferred embodiment, $R^2$ is methoxy, n is 1, $R^1$ is propyl, $Y^1$ is the residue from the reaction of a gamma-methacryloxy moiety with mercury acetate, and Z is acetate. The reactions which produce such an embodiment may be written as follows, with G designating the surface of porous glass:

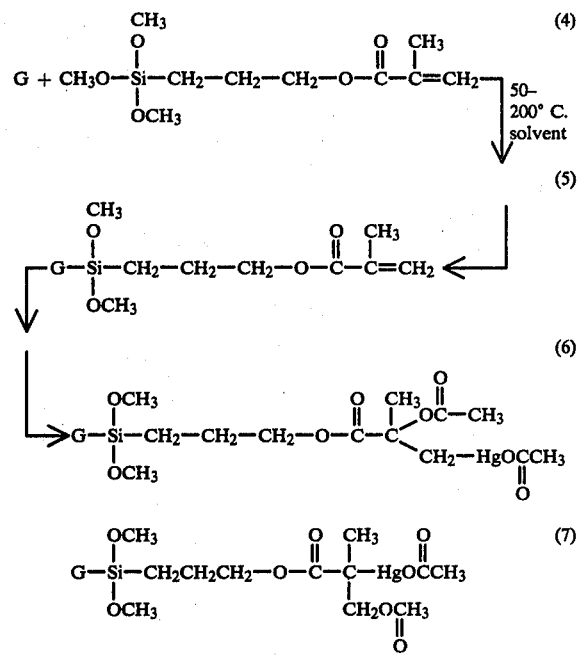

A mixture of compounds (6) and (7) is produced because of the alternate ways in which mercuric acetate can react with the double bond.

As a first step, it is preferred to clean the substrate thoroughly of any organic or inorganic contaminants. The method of cleaning may vary somewhat with different substrates, as the skilled in the art will appreciate. With porous glass, for example, typically such materials would be cleaned by washing with a dilute acid, e.g., nitric acid, sulfuric acid, hydrochloric acid, or the like, followed by removal of the acid, e.g., by rinsing, and then drying, e.g., by heating at elevated temperatures, such as 100°–700° C., preferably in vacuo.

Preferably, the powdered glass or other inorganic substrate is then treated with the coupling agent to be used. Typically this would involve treatment at high temperatures, e.g., 50°–200° C., preferably 60°–140° C., to promote the reaction between the silane and the available hydroxy or oxygen groups on the surface of the substrate. The silane coupling agent may be mixed with the high boiling solvent, and the glass beads put into contact with the solvent/silane mixture, which is maintained at reflux for a number of hours, generally between 1 and 20, preferably between 3 and 18 hours. Preferably the glass powder bearing the silane coupling agent is then cooled, filtered, washed with solvent, and dried prior to reaction with the source of mercury.

The thus prepared or "activated" glass powders are then mixed with the mercury compound of Formula 2, in a suitable solvent. Suitable solvents include alcohols and non-protic solvents such as dimethyl formamide or dimethyl sulfoxide. Preferably the solvent is a lower alcohol such as methanol or ethanol. Removal from the solvent and drying leaves a covalent mercury glass affinity product having an affinity for the sulfhydryl group.

The affinity product produced in accordance with this method can be utilized for separation of sulfhydryls from other materials. Mercury affinity columns work on the principle that sulfhydryl containing compounds such as cysteine, thiophosphates, thiolcarboxylic acid derivatives, etc. will bind to mercury atoms covalently attached to a support matrix. Generally the support matrix will be suspended in a chromatographic column, and a solution or mixture containing at least one sulfhydryl will be eluted through the column. The mercury-glass composition will bind the sulfhydryl-containing compound, thus removing it from the solution as the solution passes over the surface of the glass beads. Thereafter, the sulfhydryls contained in the column can be eluted by washing with a second sulfhydryl or by eluting a second fluid which contains mercury through the column.

The method of use of the compounds of the present invention is very straightforward. In order to use the affinity product to separate or isolate compounds having one or more sulfhydryl groups from other components of a mixture, the mixture is simply contacted with the affinity product, e.g., the preferred glass-mercury product. This may be done in a simple mixing container, with or without agitation. Conveniently it can be done by flowing a stream of the mixture past or through surfaces bearing organo-mercuric moieties in accordance with the present invention. For example, glass beads having organo-mercuric moieties bound to the surface of a coupling agent in accordance with the present invention can be packed in a known manner in a column or tube of a type typically used for chromatography, and a fluid stream carrying compounds having sulfhydryl groups can be passed through the column or tube. See, e.g., Kirk-Othmer *Encyclopedia of Chemical Technolgy*, Vol. 2, p. 586–609, Vol. 6, p. 35–54 (3rd Ed. 1979), the disclosure of which is hereby incorporated by reference. The sulfhydryl-containing compounds can then be removed from the column packing (i.e. the affinity product), e.g., by eluting another sulfhydryl-containing compound through the column which displaces the first sulfhydryl compound by competition. The sulfhydryl compound can also be removed from the column by eluting an organo-mercuric compound through the column, which will compete with and remove the sulfhydryl compound from the affinity product. Preferably both methods are employed sequentially and these steps are followed by copious rinsing of the column in order to remove all traces of organo-mercury compounds and sulfhydryl compounds, before the next sample is eluted through the column.

The invention will be further understood with reference to the following examples, which are purely exemplary in nature, and are not meant to be utilized to determine the scope of the invention.

EXAMPLE 1

100 ml of porous glass beads having pore size in the vicinity of 500A, and a particle size of about 125–177 μm were cleaned by mixing with 250 ml of 5% nitric acid, and heating to reflux for 2 hours. The porous glass beads were then cooled, filtered, washed with water (100 ml portions, 5 times) and dried in vacuo at 100° C. for 16 hours.

To the resultant dry activated glass beads were added gamma-methacryloxypropyltrimethoxy silane as a 10% solution in 250 ml of toluene. The mixture was refluxed under a nitrogen atmosphere for 18 hours, cooled, filtered, washed 6 times with 100 ml portions of chloroform, and dried in vacuo at 100° C. for 48 hours.

300 ml of 1% mercuric acetate in methanol was added to the resulting methacryloxypropl glass derivative, and stirred under a nitrogen atmosphere for 4 hours. The glass beads were then filtered and washed 4 times with 200 ml portions of methanol, and dried in vacuo at 110° C. for 16 hours, to leave a covalent mercury glass affinity support product. Analysis for mercury gave 0.14% Hg on a dry weight basis. This level of functionalization is about 7μ mol/g.

EXAMPLE 2

A chromatographic column, cylindrical in shape, having a height to diameter ratio of about 3:1, and containing 100 mg of the mercury glass beads of Example 1, is washed with four 1 ml volumes of a wash buffer. The wash buffer contains tris-hydroxymethylaminomethane ("tris") in a concentration of 50 mM in distilled water, and has a pH of about 7.6. In order to remove any previous sulfhydryl compounds from the column, the column is flushed, first with a buffer containing another sulfhydryl compound and second with a buffer containing a mercury compound. The sulfhydryl-buffer contains 50 mM Tris phosphate (pH 7.6) in distilled water, and additionally contains 2-mercaptoethanol in a concentration of 14 mM. To remove all previous sulfhydryl compounds from the column, the column is washed with five 1 ml volumes of this sulfhydryl buffer. Thereafter, the column is washed with 2 ml of a mercury buffer containing approximately 50 mM of tris (pH of about 7.6), and 10 mM of mercuric acetate (Hg(OAc)$_2$). The column is then washed with a large excess of wash buffer, e.g., 30–50 ml to remove all free mercury from the column. It is important that the mercury which is not attached to the column be removed prior to elution of the sample, lest the sample bind with the mercury that is free in the column and thereby distort the results achieved. To that end, the last portions of wash buffer from this step can be subjected to a colorimetric assay using a dye comprising potassium thiocyanide (about 20 mM) and ammonium ferricsulfate saturated in 6 N HNO$_3$ (about 100 mg in 20 ml.) By mixing this dye with the sample of the wash buffer used to wash the last amount of free mercury from the column at a ratio of about 1 to 2 and comparing that with a sample of the dye mixed with the same amount of fresh wash buffer, rather small amounts of mercury (II) (as low as about 150 μm) can be detected.

These same steps are repeated in running a sample on the column, except at first, the sample containing a sulfhydryl compound of interest is loaded on the column in approximately 1 ml of wash buffer (pH 7.6). The next step is to wash with approximately four 1 ml volumes of wash buffer in order to get the non-sulfhydryl materials out of the column. Then the sulfhydryl which binds to the column is removed by washing with five 1 ml volumes of the buffer containing 2-mercaptoethanol. Those sulfhydryls which have been bound to the column are usually removed within the first two fractions of that wash. The 2-mercaptoethanol displaces the previously bound sulfhydryl of interest, which is eluted out with the buffer. The sulfhydryls eluted from the column can be analyzed to determine how much sulfhydryl was contained in the original sample loaded on the column. Alternatively, this can be used as a very effective method of purifying the sulfhydryls. The ability to separate a sulfhydryl-containing compound from other compounds on the column permits that compound to be collected and purified.

One use of this method is the isolation of DNA fragments containing, or labeled with, a thiophosphate group.

Again the column from which the sulfhydryl material has been eluted is washed with the mercury-containing buffer to clear and revitalize the column. Finally, the column is again washed with 30–50 ml portions of wash buffer to remove the remaining free mercury, and the latter fractions of that wash buffer are preferably analyzed at least qualitatively for the presence of free mercury.

EXAMPLE 3

To 100 ml of silica gel (70–230 mesh, binder and fluorescent-free grade) add 3-aminopropyltriethoxy silane as a 10% solution in 250 ml of toluene. The mixture should be set to reflux under a nitrogen atmosphere for about 18 hours, cooled, filtered, washed six times with 200 ml portions of toluene, followed by drying in vacuo at 100° C. for 16 hours.

To a suspension of the dry silanized silica gel, add 40% aqueous DMF (250 ml) and sodium p-hydroxymercuribenzoate (6.25 g). While stirring vigorously, the pH should be adjusted to about 4.8 with HCl(12N), and N-ethyl-N$^1$(dimethylaminoethyl) carbodiimide (7.7 g) is added slowly. Allow the mixture to stir for 16 hours at room temperature. The mercury-silica gel is then filtered and washed extensively with sodium bicarbonate (0.1 M ten times 200 ml portions), and dried in vacuo at 100° C. for 16 hours.

The specific embodiments described herein are meant to be exemplary only, and various modifications will be apparent to the skilled in the art from consideration of this disclosure or practice of the invention disclosed. The claims below are intended to cover all such modifications and constitute an indication of the scope and spirit of the invention.

I claim:

1. A composition of matter comprising a metal having affinity for compounds having sulfhydryl groups, said metal being coupled covalently to an inorganic carrier having available hydroxide or oxide groups, said metal being coupled to the inorganic carrier by means of a coupling agent having a silicon portion attached to the inorganic carrier and an organic portion covalently attached to said metal, said composition of matter having the following structure:

$$G\text{-}Si(R^2)_{3-n}(R^1Y^1HgZ)_n$$

where G is the inorganic carrier, $R^1$ is alkyl, $R^2$ is lower alkoxy or halo, Z is alkyl or the conjugate base of an acid, n is an integer from 1–3, and $Y^1HgZ$ is the residue from the reaction of a substituent having the formula $$\text{-}R^1Y$$

with a compound having the formula:

$$ZHgZ'$$

where Y is selected from the group of hydroxyl, amino, substituted or unsubstituted acryloxy, isothiocyano, sulfhydryl or a diazonium salt, and Z' is alkyl, or the conjugate base of an acid, and where there are more than one Z, $Y^1$, $R^1$ or $R^2$, each may be the same or may be different.

2. The composition of claim 1, wherein the inorganic carrier is glass, colloidal silica, wollistonite, silica gell, bentonite, aluminum, hydroxy-papatite or nickel oxide.

3. The composition of claim 1, wherein the inorganic carrier is porous glass.

4. The composition of claim 1, wherein G is porous glass, Y is acryloxy or methacryloxy, $R^1$ is lower alkyl, and $R^2$ is lower alkoxy.

5. The composition of claim 5, wherein Z is acetate, halide, cyanide, hydroxide, nitrate or oxylate.

6. The composition of claim 1, where G is porous glass, $R^2$ is methoxy, n is 1, $R^1$ is n-propyl, and Y is methacryloxy.

7. The composition of claim 1, wherein $R^1$ is lower alkyl, and Y is acryloxy or methacryloxy.

8. The composition of claim 1, wherein the coupling agent is
beta-acryloxyethyltrimethoxy silane,
gamma-acryloxypropyltrimethoxy silane,
gamma-acryloxypropyl-gamma-acryloxypropyldimethoxy silane,
delta-acryloxybutyltriethoxy silane,
gamma-acryloxypropyl-gamma-methacryloxypropyl ethoxymethoxy silane,
gamma-methacryloxypropyltrimethoxy silane,
gamma-methacryloxypropyl-beta-methacryloxyethyldimethoxy silane,
or beta-methacryloxyethyl-(alpha-methyl-gamma-methacryloxypropyl)-dimethoxy silane.

9. A method of separating a sulfhydryl compound containing at least one sulfhydryl group from other compounds, comprising contacting a mixture of the sulfhydryl compound and the other compounds with an affinity product in a chromatographic column, said affinity product comprising a metal having an affinity for sulfhydryl groups, said metal being coupled covalently to an inorganic carrier having available hydroxide or oxide groups, said metal being coupled to the inorganic carrier by means of a silane coupling agent having the formula:

$$(YR^1)_n Si(R^2)_{4-n}$$

where Y is a functional group which will react with a mercuric compound, selected from hydroxyl, amino, carboxyllic acid, acyl, acyloxy, isocyano, isothiocyano, sulfhydryl or a diazonium salt; $R^1$ is alkyl, lower alkenyl, lower alkyl-aryl, or aryl; $R^2$ is selected from the group of lower alkoxy, phenoxy and halo; and n is an integer from 1 to 3, and separating such mixture from an affinity product.

10. The method of claim 9 wherein the affinity product is packed in a generally cylindrical column, and the mixture is contacted with said affinity product and separated from said affinity product by passing a fluid stream containing said mixture through the packed column.

11. The method of claim 9, wherein the silane is gamma-methacryloxypropyltrimethoxy silane, and the mercury compound is a divalent mercury salt.

12. The method of claim 9 wherein $R^1$ is lower alkyl and Y is acryloxy or methacryloxy.

13. The method of claim 9, wherein the silane coupling agent is
beta-acryloxyethyltrimethoxy silane,
gamma-acryloxypropyltrimethoxy silane,
gamma-acryloxypropyl-gamma-acryloxypropyldimethoxy silane,
delta-acryloxybutyltriethoxy silane,
gamma-acryloxypropyl-gamma-methacryloxypropyl ethoxymethoxy silane,
gamma-methacryloxypropyltrimethoxy silane,
gamma-methacryloxypropyl-beta-methacryloxyethyldimethoxy silane, or
beta-methacryloxyethyl-(alpha-methyl-gamma-methacryloxypropyl)-(dimethoxy silane.

14. A chromatographic column, comprising a generally cylindrical chamber having packing supports for supporting chromatographic packing material, said chromatographic column being packed with the organo-mercury glass composition of claim 7.

* * * * *